United States Patent [19]

Clark

[11] Patent Number: 4,909,734

[45] Date of Patent: Mar. 20, 1990

[54] APPARATUS FOR ORTHODONTIC TREATMENT

[76] Inventor: William J. Clark, 22 Hill Street, Kirkcaldy, Fife, KY1 1HX, Scotland, United Kingdom

[21] Appl. No.: 190,252

[22] Filed: May 4, 1988

[30] Foreign Application Priority Data

May 8, 1987 [GB] United Kingdom ................. 8711004

[51] Int. Cl.⁴ .............................................. A61C 7/00
[52] U.S. Cl. .................................................... 433/19
[58] Field of Search ..................... 433/5, 7, 19, 18, 20, 433/21, 11

[56] References Cited

U.S. PATENT DOCUMENTS

| 3,997,970 | 12/1976 | Hodgson | 433/19 |
| 4,245,986 | 1/1981 | Andrews | 433/5 |

Primary Examiner—Robert Peshock
Attorney, Agent, or Firm—Lynn L. Augspurger

[57] ABSTRACT

An orthodontic apparatus using an elastic member having a first and second portion fixed to anchor points which are selectively placed on anchor teeth, both anchor teeth being in the same selected dental arch and both anchor teeth on the same buccal or lingual face of the selected arch; or on the same selected posterior or anterior face of each anchor tooth. The elastic member is operative to engage and exert muscle balance, alter forces selectively either to lingual or buccal faces of the dental arches. The elastic member comprises polymer tube portions joined by bifurcated fixtures.

25 Claims, 4 Drawing Sheets

APPARATUS FOR ORTHODONTIC TREATMENT

The present invention relates to apparatus for orthodontic treatment. The present invention particularly relates to orthodontic treatment apparatus designed to alter the balance of muscular forces applied to the teeth.

Orthodontistry includes the provision of appliances for use over a period of treatment to influence growth of developing oral features or to alter the relative dispositions between existing features. Orthodontic appliances can be fixed or removeable. A fixed appliance is attached directly to teeth and pressure applied to the teeth by delivery of controlled forces to the dentition. Removeable appliances can be removed by the patient and, in the past, have generally included a rigid base plate used as a support for spring components used to apply forces to teeth. It is an object of the present invention to provide an orthodontic apparatus displaying features both of fixed and of removeable appliances.

The teeth are held in a position of equilibrium between the forces of those muscles acting upon the lips, cheeks and mandible. The forces produce a balance at some relative disposition between the mandible and the maxilla which in turn defines the relative disposition between the maxillary (upper) dental arch and the mandibular (lower) dental arch. The balance of forces thereby defines the exactness of occlusion between the upper and lower dental arches and influences the external appearance of the face. Previous appliances for influencing the balance of muscular forces have been bulky and inconvenient to the user. The present invention seeks to provide a new and convenient apparatus for improving developing dentition or facial appearance by altering the balance of forces applied to define the position of the teeth.

The present invention consists in an apparatus for orthodontic treatment comprising; a continuous elastic member having a pair of spaced fixtures dividing said elastic member into a first portion and a second portion; and anchor means for attaching each of said pair of fixtures to a respective one of a pair of anchor teeth on opposite sides of a selected one of the upper dental arch or the lower dental arch; said first portion of said elastic member being operative to engage said upper dental arch and said second portion of said elastic member being operative to engage said lower dental arch.

The present invention provides, in various embodiments, that the anchor teeth can either be both in the lower dental arch or both in the upper dental arch. Attachment of the fixtures can be either both on the buccal surfaces of the anchor teeth, both on the lingual surfaces of the anchor teeth, or both on a posterior surface of the anchor teeth. It is preferred that attachment is by way of anchor tubes attached, one to each of the anchor teeth, the anchor tubes being either both substantially parallel to the line of the gum or both substantially at ninety degrees to the line of the gum. The use of anchor tubes imparts a degree of removeability to the appliance.

The present invention further provides that the first portion of the elastic member is operative either to engage and apply forces to the inner (lingual) surface of the upper (maxillary) dental arch or to engage and apply forces to the outer (buccal) surface of the upper dental arch. When the outer surface of the upper dental arch is engaged, it is preferred that the first portion of the elastic member in fact engages the upper dental arch inside the lips in that area known as the upper vestibule, that is, the first portion of the elastic member is situated in the upper sulcus, defined as that area where the gingival tissue of the upper gums is reflected from the surface of the bone to the surface of the cheek.

The present invention further provides that, whatever the selected disposition of the first portion of the elastic member, the second portion of the elastic member is operative either to engage and apply forces to the inner (lingual) surface of the lower (mandibular) dental arch or to engage and apply forces to the outer (buccal) surface of the lower dental arch. When the outer surface of the lower dental arch is engaged it is preferred that the second portion of the elastic member in fact engages the lower dental arch inside the lips in that area known as the lower vestibule, that is, the second portion of the elastic member is situated in the lower sulcus, defined as that area where the gingival tissue of the lower gums is reflected from the surface of the bone to the surface of the cheek. The invention provides that the elastic member comprises bifurcated fixtures, each of the two fixtures having a stem and two branches. For preference, the elastic member is formed from polymer tube and the branches are inserted, one into the first portion and one into the second portion of the elastic member, so that the two portions of the elastic member and the two bifurcated fixtures then form a continuous, endless whole. The stems of the bifurcated fixtures can then be inserted into the anchor tubes and either fixedly or removeably attached to the anchor tubes.

The bifurcated fixtures can be shaped so that the first portion and second portion of the elastic member can selectably each engage either the inner or the outer surfaces of their respective dental arches.

The present invention further provides that stems of the bifurcated fixtures can be inserted into either end of the anchor tubes to select the magnitude, balance of forces and center of force for the appliance.

The present invention is further explained, by way of an example, by the following description, taken in conjunction with the appended drawings, in which.

Figure 11:
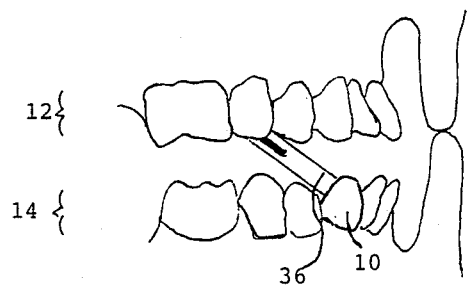

FIG. 11 a side view of the dentition showing the elastic member engaging the inner surfaces of the upper and lower dental arches with the anchor teeth in the upper dental arch.

Figure 12:
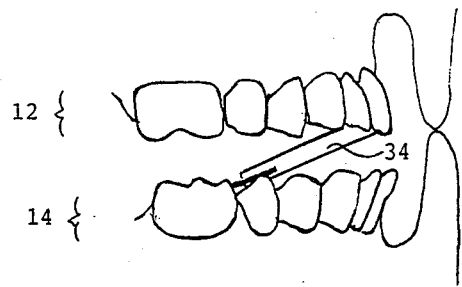

FIG. 12 is a side elevation of the dentition illustrating the elastic member engaging the inner surfaces of the upper and lower dental arches with the anchor teeth in the lower dental arch.

Figure 13:
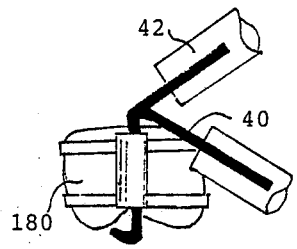

FIG. 13 shows how the stems of the bifurcated fixtures can be placed in a first end of the anchor tubes to establish a first position for the appliance.

Figure 14:
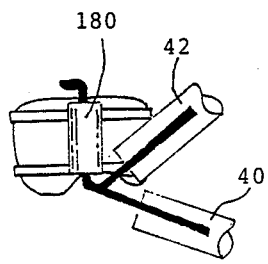

FIG. 14 shows how the stems of the bifurcated fixtures can be placed in a second end of the anchor tubes to eastablish a second position for the appliance.

Figures 3A, 4A, 5A:
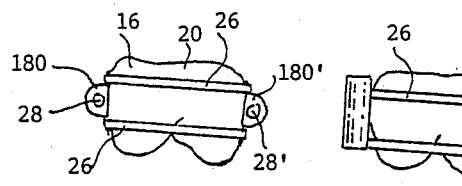
FIGS. 3A and 3B illustrate how an anchor tube is affixed to the buccal or lingual surface of an anchor tooth, parallel to the gums.
FIGS. 4A and 4B illustrate how an anchor tube is affixed to the buccal or lingual surfaces of an anchor tooth, substantially at ninety degrees to the gums.
FIGS. 5A and 5B illustrate how an anchor tube is affixed to the posterior surface of an anchor tooth, substantially at ninety degrees to the gums.
Figure 5B:
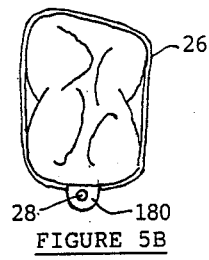
Figure 15A:
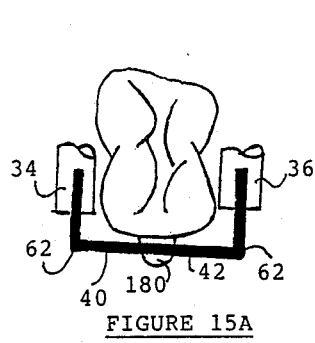
Figure 15B:
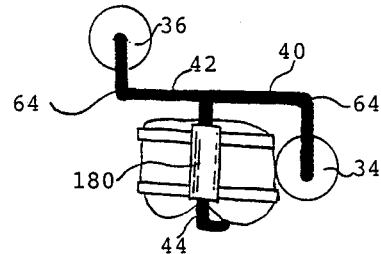
Figure 15C:
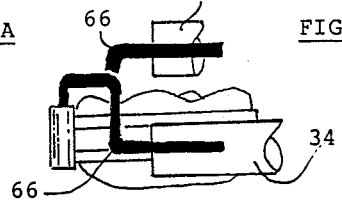

FIGS. 15A and 15B and 15C illustrate how the posterior mount of FIGS. 5A and 5B, together with shaping or forming of the bifurcated fixtures, can be used to allow engagement of the inner surface of one dental arch and of the outer surface of the other dental arch.

Figure 1:
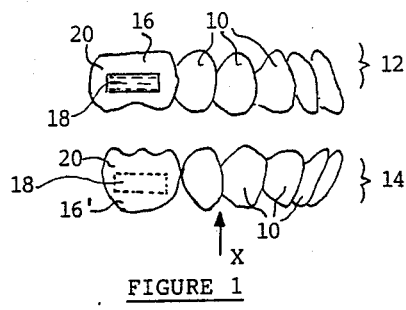
FIG. 1 shows a side elevation of the developing human dentition and illustrates attachment of anchor tubes.

FIG. 1 shows the developing human dentition in side elevation. The teeth 10 are divided into two dental arches, the upper (or maxillary) dental arch 12 comprising those teeth in the maxilla (commonly called the upper jaw), and the lower (or mandibular) dental arch 14 comprising those teeth in the mandible (commonly called the lower jaw). Two anchor teeth 16 are selected, both in the same dental arch 12 14. An anchoring device 18 is affixed, one to each anchor tooth 16, in a manner hereinafter described, ready to receive an orthodontic appliance.

The present invention provides that the anchoring devices 18 can be affixed virtually to any selected pair of anchor teeth 16 in the same dental arch 12 14. In the figures, the anchoring devices 18 are shown as affixed, in each example, to the final molar 20 of the respective dental arch 12 14. It is to be understood that the invention is not limited by this manner of illustration, and that other teeth 10 anterior to the final molars 20 in each dental arch 12 14 can be used as anchor teeth 16.

Figure 2:
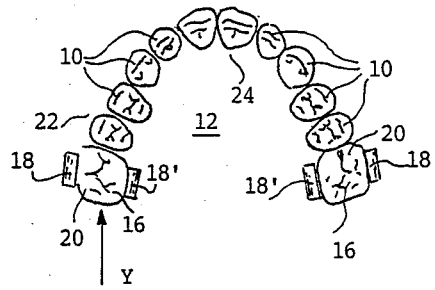
FIG. 2 is a plan view (taken in the direction of the arrow X of FIG. 1) of the upper or maxillary dental arch and further illustrates fixing of anchor tubes.

The anchor teeth 16 are shown in FIGS. 1 and 2 as being in the upper dental arch 12. It is to be understood that the anchor teeth 16 can also be in the lower dental arch 14. FIG. 1 shows, in phantom outline, an alternative anchoring device on one of a pair of anchor teeth 16' in the lower dental arch 14, it again being understood that teeth 10, anterior to the final molar 20 in the lower dental arch 14, can also be selected as anchor teeth.

While the invention is illustrated in the drawings as being applied to immature and developing human dentition, it is to be understood that this is done purely by way of example, that the invention is not limited by this example, and that the invention can equally be applied to treatment of mature dentition.

FIG. 2 shows a plan view (from below) of the upper dental arch 12 viewed in the direction of the arrow X in FIG. 1.

The upper dental arch 12 comprises an arcuate array of teeth 10 presenting an outer (or buccal) surface 22 to the interior of the cheeks, and an inner (or lingual) surface 24 to the tongue. Each tooth 10 20 comprises a buccal face towards the cheeks (not shown), a lingual face towards the tongue (not shown), an anterior face towards the front of the mouth, and a posterior face towards the rear of the mouth. It is to be understood that exactly the same notation is employed to describe the lower dental arch 14.

The anchor devices 18 are mounted both on the same face 22 24 of the upper dental arch. In a first position, anchor devices 18 are mounted on the buccal surface of the anchor teeth 20. In an alternative position, anchor devices 18' can be mounted on the lingual faces of the anchor teeth 20. When the lower dental arch 14 is selected, corresponding alternatives exist. The embodiments of the present invention hereinafter described show the anchor teeth 20 in the same dental arch 12 14, and opposed to one another in the selected dental arch (i.e., they are corresponding teeth on either side of the dental arch 12 14.) The described embodiments show a minimum of two anchor devices 18 18', both anchored either to the same face 22 24, buccal, lingual, anterior or posterior, of their respective anchor teeth 20. It is to be understood that the present invention also provides, by adaptation over those embodiments shown, such adaptations being clear to one skilled in the art, for provision of anchor devices 18 18' not on the same faces 22 24 of their respective anchor teeth 20 and for anchor teeth not exactly opposed in their dental arch 12 14.

Figure 3B:
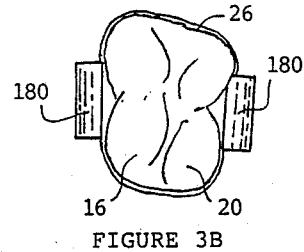

FIG. 3A shows an elevation of one the lefthand final molars 20 of FIG. 2, viewed in the direction of the arrow Y so that its posterior face is visible, and FIG. 3B shows a plan view of the same tooth 20. The molar 20 is chosen as an anchor tooth 16 and the anchor device provided in the form of anchor tube 180 180' attached to the anchor tooth 16 by encircling metal bands 26. As will later become clear, only one anchor tube 180 180' is required. A buccal anchor tube 180 can be provide on the buccal surface of the anchor tooth. Alternatively, in those embodiments where lingual anchoring is required, a lingual anchor tube 180' is provided. It is also possible to provide both anchor tubes 180 180' for use where the anchor point of the appliance will require to be changed from time to time. In this instance the anchor tubes are substantially parallel to the gums. Each anchor tube 180 180' is penetrated by a an anchor channel 28 28' passing through the entirety of its length.

Figure 4B:
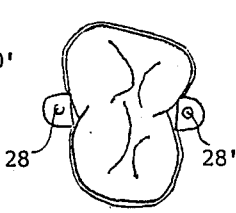

FIG. 4A corresponds to FIG. 3A and FIG. 4B corresponds to FIG. 3B, with the exception that the anchor tubes 180 180' are mounted substantially at ninety degrees to the gum for use in those instances where a buccal or lingual appliance mount is required in this attitude.

FIG. 5A corresponds to FIG. 3A and FIG. 5B corresponds to FIG. 3B with the exception that the anchor tube 180 is provided on the posterior face of the anchor tooth for use in those circumstances, as will later be described, where the appliance is to engage the buccal surface 22 of one dental arch 12 14 and the lingual surface of the other dental arch 12 14. It is to be understood that, if space permits, and if required, a single anchor tube 180 can be mounted on the anterior face 32 of anchor tooth.

Figure 6:
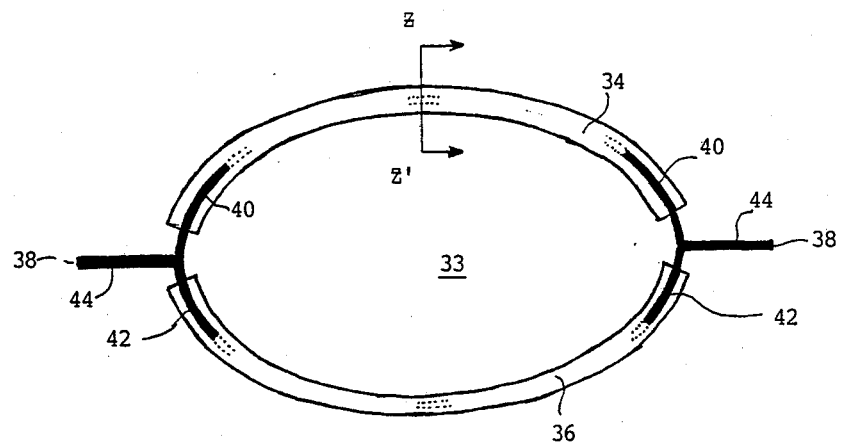
FIG. 6 shows the construction of the elastic member.

FIG. 6 shows the elastic member 33 of the appliance.

A first vermiform portion 34 is joined at either end to a second vermiform portion 36 by a pair of bifurcated fixtures 38 comprising a first branch 40, a second branch 42, and a stem 44.

Figure 7:
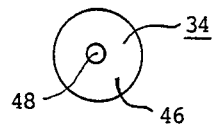
FIG. 7 shows a cross section through the elastic member along the line Z–Z' of FIG. 6, looking in the direction of the arrows.

FIG. 7 shows a cross section of the first vermiform portion 34 taken along the line Z-Z', looking in the direction of the arrows. The first portion 34 is formed from a hollow polymer tube 46 of elastic material and having a central cavity 48 running along its length. The second portion 36 is made in the same way. The elastic member 33 is put together by inserting the first branch 40 of each bifurcated fixture 38 into the cavity 48 of the tube 46 of the first portion 34 at either end, and by inserting the second branch 42 of each bifurcated fixture 38 into the cavity 48 at either end of the second portion 36. The first 34 and second 36 portions and the two bifurcated fixtures 38 combine to render the elastic member 33 continuous and the protuding stems 44 are each inserted into their respective anchor channel 28 to fix the elastic member 33 in the mouth.

The polymer tube 46 can be any elastic polymer suitable to provide, as hereinafter described, a predetermined, selected and controlled elastic force to the dental arches. Polyvinylchloride of 0.4 cm external diameter has been found suitable. Silicon rubber tube has also been found of utility. The elastic force of the tube 46 on the branches 40 42 has been found sufficient to ensure retention for all practical purposes where around 1.0 cm penetration in the cavity 48 has been provided. It is possible, if short penetration in the cavity 48 is necessary, or if high stress is envisaged for a particular use, to glue the branches 40 42 into the cavity 48. Those skilled in the art will be aware of other materials which can be adapted to such use and other methods, such as roughening or tip bending, for keeping the branches 40 42 in the cavity 48.

The fixtures 38 are of metal and, for preference, can be bent during installation of the appliance to achieve optimum positioning for the first 34 and second portions 36.

Figure 8:
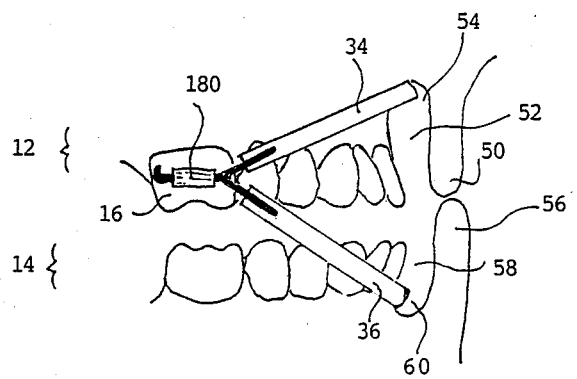
FIG. 8 shows the elastic member engaging the outer surfaces of the upper and lower dental arches with the anchor teeth in the upper dental arch.

FIG. 8 shows one manner in which the invention can be installed in the mouth. Horizontal anchor tubes 180 are fixed to buccal faces of anchor teeth 16 in the upper dental arch 12. The stems 44 of the bifurcated fixtures 38 are passed through the anchor channels 28 of their respective anchor tubes and either bent over at the protuding end (as shown) or fixed against re-emergence by means of a bead being firmly attached to their ends. In those instances where the appliance is to be removeable, removeable attachments by bead or screw can be made to the ends of the stems 44 allowing subsequent removal of the stem 44 from the anchor channel 28. Alternatively, the stems 44 and the anchor tubes 180 can be so angled, when installed, that the elastic forces from the elastic member retain the stems 44 in the channels, so that the appliance is removeable after elastic force release.

The first portion 34 of the elastic member 33 engages the buccal surface 22 of the upper dental arch 12 and the second portion 36 of the elastic member 33 engages the buccal surface 22 of the lower dental arch. For preference, the first portion 34 of the elastic member 33 is situated behind the upper lip 50 in an area known as the upper vestibule 52 and occupies the upper sulcus 54 where the upper gingival tissue is reflected from the bone towards the cheek. Also for preference, the second portion 36 of the elastic member 33 is situated behind the lower lip 56 in an area known as the lower vestibule 58 and occupies the lower sulcus 60 where the lower gingival tissue is reflected from the bone of the mandible towards the cheeks.

The lengths of the first 34 and second 36 portions of the elastic element 33 can be selected to exert a selectable amount of force depending upon the dimensions of the mouth to be treated and the strengths and directions of additional force which are required. The example shown in FIG. 8 exerts pulls towards the centre of additional force, i.e. towards the position of the mounting tubes 180.

Figure 9:
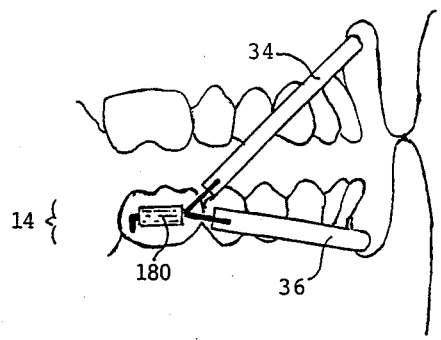
FIG. 9 shows the elastic member engaging the outer surfaces of the upper and lower dental arches with the anchor teeth in the lower dental arch.

FIG. 9 shows the same view as FIG. 8, but illustrates another way the invention can be installed, this time with the anchor tubes 180 on the buccal face 22 of the lower dental arch 14 and with different tensions and directions of pull in the first 34 and second portions 36 of the elastic element 33 by virtue of the altered centre of pull.

Figure 10:
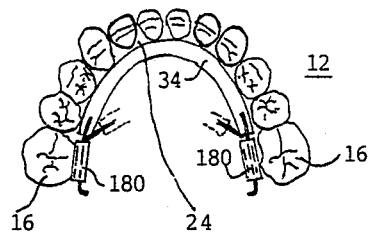
FIG. 10 is a plan view of the upper dental arch, illustrating how the elastic member engages the inner or lingual surface of the upper dental arch.

FIG. 10 shows how the elastic member 33 can be mounted to engage the lingual surface 24 of a dental arch 12 14. The upper dental arch 12 is shown in plan view, by way of illustration, it being understood that the lower dental arch 14 can be similarly treated. The anchor tubes 180 are mounted on the lingual surfaces of their respective anchor teeth 16 and the first portion 34 of the elastic member 33 urged in compression against the lingual surface 24 of the upper dental arch 12. Once again, the amount of force exerted by the first portion 34 of the elastic member 33 is determined by selection of length and material of the first portion 34.

FIG. 11 shows the view of FIGS. 8 and 9, this time illustrative of yet a further manner of application of the appliance. The anchor tubes 180 are attached on the lingual face 24 of the upper dental arch 12. The first portion 34 of the elastic member 33 is in engagement with the lingual face 24 of the upper dental arch 12 and is hidden from view. The second portion 36 of the elastic member 33 extends from the anchor tubes 180 into engagement with lingual surface 24 of the lower dental arch 14. Other anchor means, known in the art, may be employed, if required, to anchor the second portion 36 of the elastic element 33 in engagement with the lower dental arch 14. For example, loop and attachments can be applied to selected teeth to prevent the second portion 36 from lifting out of the lower dental arch 14 on extremes of mandibular extension.

FIG. 12 shows the same situation as FIG. 11, except that, in this yet further manner of application of the appliance, the anchor tubes 180 are provided on the lingual surface 24 of the lower dental arch 14. This time the roles of the two dental arches 12 14 are reversed.

The embodiments of FIGS. 11 and 12 allow application of controlled resistance to occlusion between the dental arches 12 14 with selectable centre and magnitude of force.

FIGS. 13 and 14 show how the vertical anchor tubes 180, substantially by ninety degrees to the gums, first shown in FIGS. 4 and 5, can be used to replace the anchor tubes 180, substantially parallel to the gums, discussed in relation to FIGS. 8, 9, 11 and 12. When a different centre of additional force is required, the stems 44 can be inserted at either end of the anchor tube 180 of FIGS. 13 and 14, to select a high or a low centre. Likewise, if an anchor tube parallel to the gum is used, either end may be employed as the entry point for the stems 44. The bifurcated fixtures 38 are shaped or bent to optimum shape for each selected centre of additional force.

FIG. 15A corresponds to FIG. 5A and FIG. 15B corresponds to FIG. 5B. FIG. 15C is a side elevation of FIGS. 15A and 15B. FIGS. 15A, 15B and 15C combine to illustrate the manner in which the bifurcated element 38 can be bent, when in the posteriorly mounted anchor tube 180, to permit one portion 34 36 of the elastic member 33 to engage the the buccal face 22 of its respective dental arch 12 14 and the other portion 36 34 of the elastic member 33 to engage the lingual face of its respective dental arch 14 12. The branches 40 42, initially directed one towards the lingual side 24 and one towards the buccal side 22 of the dental arch 12 14, are each provided with a first bend 62 in the direction of the dental arch, a second bend 64 at a right angle to the plane of the dental arch 12 14, and a third bend 66 once more into the line of the dental arch 12, 14. This carries one portion 34 36 of the elastic member 33 to the buccal side 24 of the dental arch 12 14 and the other portion 36 34 of the elastic member 33 to the lingual side 22 of the dental arch 12 14, each for engagement with the side 22 24 of their respective dental arch 12 14 on which they have been placed.

I claim:

1. An apparatus for orthodontic treatment comprising; a continuous elastic member having a pair of spaced fixtures dividing said elastic member into a first portion and a second portion; and anchor means for attaching each of said pair of fixtures to a respective one of a pair of anchor teeth on opposite sides of a selected one of the upper dental arch or the lower dental arch; said first portion of said elastic member being operative to engage said upper dental arch and said second portion of said elastic member being operative to engage said lower dental arch.

2. An apparatus according to claim 1 for use where said anchor teeth are in said lower dental arch.

3. An apparatus according to claim 2 wherein said first portion of said elastic member is operative to engage the lingual surface of said upper dental arch and wherein said second portion of said elastic member is operative to engage the lingual surface of said lower dental arch.

4. An apparatus according to claim 2 wherein said first portion of said elastic member is operative to engage the buccal surface of said upper dental arch and wherein said second portion of said elastic member is operative to engage the buccal surface of said lower dental arch.

5. An apparatus according to claim 2 wherein said first portion of said elastic member is operative to engage the lingual surface of said upper dental arch and wherein said second portion of said elastic member is operative to engage the buccal surface of said lower dental arch.

6. An apparatus according to claim 2 wherein said first portion of said elastic member is operative to engage the buccal surface of said upper dental arch and wherein said second portion of said elastic member is operative to engage the lingual surface of said lower dental arch.

7. An apparatus according to claim 4 wherein said buccal surface of said lower dental arch includes the lower vestibule.

8. An apparatus according to claim 5 wherein said buccal surface of said lower dental arch includes the lower vestibule.

9. An apparatus according to claim 5 wherein said buccal surface of said upper dental arch includes the upper vestibule.

10. An apparatus according to claim 6 wherein said buccal surface of said upper dental arch includes the upper vestibule.

11. An apparatus according to claim 1 for use where said anchor teeth are in said upper dental arch.

12. An apparatus according to claim 11 wherein said first portion of said elastic member is operative to engage the lingual surface of said upper dental arch and wherein said second portion of said elastic member is operative to engage the lingual surface of said lower dental arch.

13. An apparatus according to claim 11 wherein said first portion of said elastic member is operative to engage the buccal surface of said upper dental arch and wherein said second portion of said elastic member is operative to engage the buccal surface of said lower dental arch.

14. An apparatus according to claim 11 wherein said first portion of said elastic member is operative to engage the lingual surface of said upper dental arch and wherein said second portion of said elastic member is operative to engage the buccal surface of said lower dental arch.

15. An apparatus according to claim 11 wherein said first portion of said elastic member is operative to engage the buccal surface of said upper dental arch and wherein said second portion of said elastic member is operative to engage the lingual surface of said lower dental arch.

16. An apparatus according to claim 13 wherein said buccal surface of said lower dental arch includes the lower vestibule.

17. An apparatus according to claim 14 wherein said buccal surface of said lower dental arch includes the lower vestibule.

18. An apparatus according to claim 12 wherein said buccal surface of said upper dental arch includes the upper vestibule.

19. An apparatus according to claim 13 wherein said buccal surface of said upper dental arch includes the upper vestibule.

20. An apparatus according to claim 1 wherein said elastic member is a polymer band.

21. An apparatus according to claim 1 wherein said spaced fixtures each comprise a bifurcated member having a stem and first and second branches; said first branch being inserted into an end of said first portion of said elastic member; said second branch being inserted into an end of said second portion of said elastic member; and fixtures co-operating to render said elastic member continuous; and said stem being attached to said anchor means.

22. An apparatus according to claim 21 wherein said elastic member is a polymer band.

23. An apparatus according to claim 1 wherein said anchor means comprises one or more anchor tubes attached to the anchor teeth.

24. An apparatus according to claim 1 wherein said spaced fixtures each comprise a bifurcated member having a stem and first and second branches; said first branch being inserted into an end of said first portion of said elastic member; said second branch being inserted into an end of said second portion of said elastic member; said fixtures co-operating to render said elastic member continuous; and said stem being attached to said anchor means, and wherein said one or more anchor tubes are adapted to receive said stem in said each fixture.

25. An apparatus according to claim 1 wherein said anchor teeth on said opposite sides of said selected dental arch are corresponding teeth on said opposite sides of said selected dental arch.

* * * * *